United States Patent [19]

Aberg et al.

[11] Patent Number: 5,061,694
[45] Date of Patent: Oct. 29, 1991

[54] METHOD FOR STABILIZING OR CAUSING REGRESSION OF ATHEROSCLEROSIS IN CORONARY ARTERIES EMPLOYING AN ACE INHIBITOR

[75] Inventors: A. K. Gunnar Aberg, Lawrenceville; Patricia Ferrer, Pennington; Miguel A. Ondetti, Princeton, all of N.J.

[73] Assignee: E. R. Squibb & Sons, Inc., Princeton, N.J.

[21] Appl. No.: 426,139

[22] Filed: Oct. 23, 1989

[51] Int. Cl.$^5$ ................ A61K 31/40; A61K 31/66; A61K 37/00
[52] U.S. Cl. ................................... 514/19; 514/114; 514/423
[58] Field of Search ................... 514/423, 19, 114

[56] References Cited

U.S. PATENT DOCUMENTS 4,316,906 2/1982 Ondetti et al. ................ 424/274

FOREIGN PATENT DOCUMENTS 0219782 10/1986 European Pat. Off.

OTHER PUBLICATIONS

Overturf, M., et al., Atherosclerosis, 59:383–399, 1986.
Zorn, J., et al., "Prevention of Arteriosclerotic Lesions with Calcium Antagonists or Captopril in Different Rat Hypertension Models," J. Cardiovasc. Pharmacol., vol. 12 (Suppl 6), (1988).
Someya, N., et al., "Suppressive Effect of Captopril on Platelet Aggregation in Essential Hypertension," J. Cardiovasc. Pharmacol., 6:840–843 (1984).
Mizuno, K., et al., "The Effects of the Angiotensin I-Converting Enzyme Inhibitor, Captopril, on Serum Lipoperoxides Level and the Renin-Angiotensin-Aldosterone and Kallikrein-Kinin Systems in Hypertensive Patients," Nippon Naibunpi Gakkai Zasshi, Fef. 20, 1984.
Mizuno, K., et al., "Acute Effects of Captopril on Serum Lipid Peroxides Level in Hypertensive Patients," Tohoku J. Exp. Med., May, 1984, 143(1) pp. 127–128.
Cecil, Textbook of Medicine, 16 Ed., pp. 239–241.

*Primary Examiner*—Stanley J. Friedman
*Attorney, Agent, or Firm*—Burton Rodney

[57] ABSTRACT

A method is provided for slowing the progression of atherosclerosis in coronary arteries in hypertensive or normotensive patients and reducing or eliminating atherosclerotic lesions in such patients in a mammalian species by administering an ACE inhibitor, especially one containing a mercapto moiety, such as captopril or zofenopril.

18 Claims, No Drawings

METHOD FOR STABILIZING OR CAUSING REGRESSION OF ATHEROSCLEROSIS IN CORONARY ARTERIES EMPLOYING AN ACE INHIBITOR

FIELD OF THE INVENTION

The present invention relates to a method for stabilizing or causing regression of atherosclerosis in coronary arteries in mammalian species by administering an ACE inhibitor, preferably an ACE inhibitor containing a mercapto moiety, such as captopril or zofenopril.

BACKGROUND OF THE INVENTION

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

Zorn, J. et al, "Prevention of Arteriosclerotic Lesions with Calcium Antagonists or Captopril in Different Rat Hypertension Models," J. Cardiovasc. Pharmacol. Vol. 12 (Suppl 6), 1988, discloses beneficial effects in mesenteric arteries atherosclerosis with captopril in spontaneous hypertensive Okamoto rats (SHRs), but not in salt-sensitive Dahl rats.

Someya, N. et al, "Suppressive Effect of Captopril on Platelet Aggregation in Essential Hypertension," J. Cardiovasc. Pharmacol. 6:840–843, 1984, discloses at page 840 that "hypertension is closely related to the genesis and progress of atherosclerosis," and that "platelet function plays an important role in atherosclerosis, with platelet dysfunction demonstrable in several vascular diseases. It has been reported that platelet aggregation is increased in hypertensives . . . ." At page 842, it is indicated that the "data demonstrated the inhibition of platelet aggregation in vivo after administration of captopril to hypertensive subjects . . . ." At page 843, it is indicated that "platelet aggregability is greater in hypertensives than in normotensives . . . platelet abnormalities may be a risk factor in atherosclerosis . . . . If captopril possesses an antiplate aggregability effect in addition to its hypotensive effect, it may be very useful for the prevention of atherosclerosis and thrombotic diseases associated with hypertension."

Mizuno, K. et al "The effects of the angiotensin I-converting enzyme inhibitor, captopril, on serum lipoperoxides level and the renin-angiotensin-aldosterone and kallikrein-kinin systems in hypertensive patients," Nippon Naibunpi Gakkai Zasshi, Feb. 20, 1984, discloses that captopril is a beneficial antihypertensive agent for preventing serum lipoperoxides concentration (LPX)-induced atherosclerosis in hypertensive patients.

Mizuno, K. et al "Acute effects of captopril on serum lipid peroxides level in hypertensive patients," Tohoku J. Exp. Med., May, 1984, 143(1) p. 127-8, suggests that inhibition of angiotensin-converting enzyme by captopril offers a possible therapeutic approach to the treatment of atherosclerosis complicated with hypertension.

The role of the renin-angiotensin system in atherosclerosis is not clear. Campbell-Boswell & Robertson, Exp. and Mol. Pathol. 35:265 (1981) reported that angiotensin II stimulated proliferation of isolated human vascular smooth muscle cells while Geisterfer et al, Circ. Res. 62: 749–756 (1988) showed no proliferation (but stimulation of growth) of isolated rat vascular smooth muscle cells.

Overturf, M. et al, Atherosclerosis, 59:283–299, 1986, discloses that studies with ACE inhibitors in cholesterol fed rabbits show no significant effects in the development of atherosclerosis.

Cecil, Textbook of Medicine, 16 Ed., pp 239 to 241, indicates at page 240 that blood pressure is an accelerator of atherosclerosis.

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-pnehylbutyl)phosphinyl]-oxy]-1 -oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

It has now been found that angiotensin converting enzyme inhibitors, especially mercapto containing ACE inhibitors such as captopril and zofenopril, are capable of stabilizing atherosclerosis by slowing the progress thereof, and even reducing and reversing atherosclerotic lesions, in coronary arteries.

DESCRIPTION OF THE INVENTION

In accordance with the present invention, a method is provided for slowing the progress of atherosclerosis in coronary arteries and even reducing and regressing atherosclerotic lesions in coronary arteries, in mammalian species, wherein a therapeutically effective amount of an angiotensin converting enzyme inhibitor is administered systemically, such as orally or parenterally.

The ACE inhibitor may be administered to hypertensive patients or normotensive patients in accordance with the method of the present invention.

In preferred embodiments, mercapto (—S—) containing ACE inhibitors are employed in the method of the invention. It is theorized that mercapto containing ACE inhibitors prevent oxidation of low density lipoprotein (LDL) so that it will not be taken up by tissue marophages to generate the fatty-streak lesion of atherosclerosis. However, there may be other mechanisms through which these ACE inhibitors exert their anti-atherosclerotic effects.

The phrase "stabilizing" atherosclerosis as used herein refers to slowing down the development of atherosclerosis and/or inhibiting formation of new atherosclerotic lesions.

The phrase "causing regression of" atherosclerosis as used herein refers to reducing and/or eliminating atherosclerotic lesions.

The fact that in accordance with the method of the invention ACE inhibitors stabilize or slow down atherosclerosis in the coronary arteries and may even reduce or eliminate (regression) atherosclerosis of atherosclerotic lesions in the coronary arteries regardless of whether the patient is hypertensive of normotensive is especially surprising. Until now, any suggestion for use of ACE inhibitors for treating atherosclerosis has been made in conjunction with atherosclerosis in hypertensive patients. Furthermore, it has never been previously recognized that ACE inhibitors are especially effective in treating coronary arteries and even effect regression of atherosclerosis in coronary arteries of either hypertensive or normotensive patients.

The angiotensin converting enzyme inhibitor which may be employed herein preferably includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

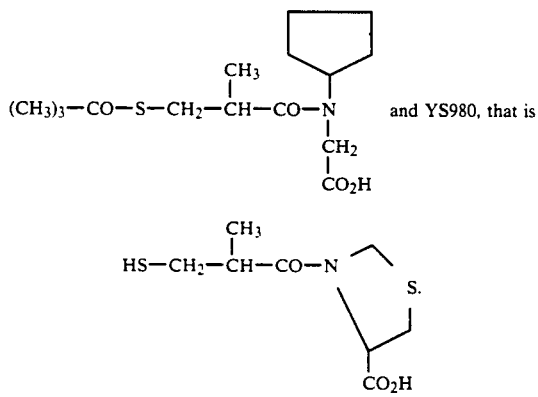

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-(1-ethoxycarbonyl-3-phenyl-(1S)-propyl]amino)-2,3,4,5-tetrahydro-2-oxo-1-(3S) -benzazepine-1 acetic acid HCl) disclosed in U.K. Patent No. 2103614 and CGS 16,617 (3(S)-[[(1S)-5-amino1-carboxypentyl-]amino]-2,3,4,5-tetrahydro-2-oxo -1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl ]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, the angiotensin converting enzyme inhibitor may be administered to mammalian species, such as horses, cattle, dogs, cats, and humans, and as such may be incorporated in a conventional systemic dosage form, such as a tablet, capsule, elixir or injectable, as well as suppository dosage forms that release ACE inhibitor in the bloodstream. The above dosage forms will also include the necessary carrier material, excipient, lubricant, buffer, bulking agent (such as mannitol), antioxidants (ascorbic acid of sodium bisulfite) or the like. Oral dosage forms are preferred, although parenteral forms such as intramuscular, intraperitoneal, or intravenous enema and suppository forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg.

A preferred oral dosage form, such as tablets or capsules, will contain the ACE inhibitor in an amount of from about 0.1 to about 500 mg, preferably from about 5 to about 200 mg, and more preferably from about 10 to about 150 mg.

For parenteral administration, the ACE inhibitor will be employed in an amount within the range of from about 0.005 mg/kg to about 10 mg/kg and preferably from about 0.01 mg/kg to about 1 mg/kg.

The composition described above may be administered in the dosage forms as described above in single or divided doses of one to four times daily. It may be advisable to start a patient on a low dose and work up gradually to a high dose.

Tablets of various sizes can be prepared, e.g., of about 50 to 700 mg in total weight, containing the active substance in the range described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance in a conventional liquid vehicle acceptable for pharmaceutical administration so as to provide the desired dosage in one to four teaspoonfuls.

Such dosage forms can be administered to the patient on a regimen of one to four doses per day.

Suppository formulations containing from about 5 to about 250 mg ACE inhibitor may be prepared as well using a conventional suppository base (such as disclosed in U.S. Pat. Nos. 4,344,968, 4,265,875, and 4,542,020) so as provide the desired dosage in one to four suppositories per day.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

The formulations as described above will be administered for a prolonged period, that is, for as long as it is necessary to treat the atherosclerosis. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLE 1

A captopril formulation suitable for oral administration in slowing the progression of atherosclerosis in coronary arteries in hypertensive or normotensive patients and reducing or eliminating coronary atherosclerotic lesions in such patients is set out below.

1000 tablets each containing 100 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 100 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating atherosclerosis as described above.

EXAMPLE 2

1000 tablets each containing 200 mg of captopril are produced from the following ingredients:

| | |
|---|---|
| Captopril | 200 g |
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in slowing the progression of atherosclerosis in coronary arteries in hypertensive or normotensive patients and reducing or eliminating coronary atherosclerotic lesions in such patients.

EXAMPLE 3

Two piece #1 gelatin capsules each containing 250 mg of captopril are filled with a mixture of the following ingredients:

| | |
|---|---|
| Captopril | 250 mg |
| Magnesium stearate | 7 mg |
| USP lactose | 193 mg |

The resulting capsules are useful in slowing the progression of atherosclerosis in coronary arteries in hypertensive or normotensive patients and reducing or eliminating coronary atherosclerotic lesions in such patients.

EXAMPLE 4

An injectable solution for use in slowing the progression of atherosclerosis in coronary arteries in hypertensive or normotensive patients and reducing or eliminating coronary atherosclerotic lesions in such patients.

| | |
|---|---|
| Captopril | 500 mg |
| Methyl paraben | 5 mg |
| Propyl paraben | 1 mg |
| Sodium chloride | 25 g |

-continued

| Water for injection qs. | 5 l. |
|---|---|

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 5 to 8

Dosage forms for use in slowing the progression of atherosclerosis in coronary arteries in hypertensive or normotensive patients and reducing or eliminating coronary atherosclerotic lesions in such patients are prepared as described in Examples 1 to 4 except that N-(1-ethoxycarbonyl-3-phenylpropyl)-L-alanyl-L-proline (enalapril) is used in place of captopril.

EXAMPLE 9 and 10

A suppository formulation containing conventional suppository base such as any of those disclosed in U.S. Pat. Nos. 4,344,968, 4,265,875 or 4,542,020, and N-(1-ethoxy-carbonyl-3-phenylpropyl)-L-alanyl-L-proline (40 mg), (enalapril) or captopril (25 mg), is prepared and is used to slowing the progression of atherosclerosis in coronary arteries in hypertensive or normotensive patients and reducing or eliminating coronary atherosclerotic lesions in such patients.

EXAMPLE 11

A zofenopril formulation suitable for oral administration in slowing the progression of atherosclerosis in coronary arteries in hypertensive or normotensive patients and reducing or eliminating coronary atherosclerotic lesions in such patients is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating atherosclerosis as described above.

EXAMPLE 12

A modified release beadlet formulation capable of slowly releasing the angiotensin converting enzyme inhibitor captopril over a period of up to 6 hours and having the following composition was prepared as described below.

| Ingredient | Amount in Parts by Weight |
|---|---|
| Captopril | 27 |
| Citric acid | 30 |
| Microcrystalline cellulose* | 43 |

*amount may vary to reflect chemical purity of captopril

The above ingredients were mixed and kneaded using water in a planetary mixer to form a wet mass. The wet mass was passed through a Nica E140 extruder to form an extrudate (~1 mm diameter). The extrudate was then passed through a Nica spheronizer to form beadlets. The beadlets were then dried at 40° C. for 12–18 hours in a tray drying oven or for 2–4 hours in a fluid bed dryer. A fraction of the so-formed beadlets were filled into hard shell pharmaceutical capsules for use in slowing the progression of atherosclerosis in coronary arteries in hypertensive or normotensive patients and reducing or eliminating coronary atherosclerotic lesions in such patients.

EXAMPLE 13

A modified release coated-beadlet formulation having the following composition was prepared as follows.

| | | | mg/dose |
|---|---|---|---|
| (i) | Core | | |
| | Captopril | | 100 mg |
| | Microcrystalline cellulose | | 159.1 mg |
| | Citric acid | | 37. mg |
| | Lactose | | 74.1 mg |
| (ii) | Sealcoat | | |
| | Hydroxypropyl methyl cellulose | ca. | 8.3 mg |
| | Polyethylene glycol | ca. | 2.8 mg |
| (iii) | Barriercoat | | |
| | Cellulose acetate phthalate | ca. | 4.2 mg |
| | Acetylated monoglycerides (Myvacet ®9–40) | ca. | 1.3 mg |

The beadlet cores were prepared as described in Example 12. After the dried beadlets were formed, they were coated via a two step process as follows. An aqueous solution of hydroxypropyl methyl cellulose (7.5% by weight) and polyethylene glycol (2.5% by weight) was prepared and sprayed on to the beadlets to form a sealcoat. The beadlets were then coated with a barriercoat using an aqueous dispersion of cellulose acetate phthalate (30% by weight) mixed with acetylated monoglycerides (9.5% by weight). The beadlets were then filled into hard shell pharmaceutical capsules which are useful in slowing the progression of atherosclerosis in coronary arteries in hypertensive or normotensive patients and reducing or eliminating coronary atherosclerotic lesions in such patients.

EXAMPLE 14

A modified release coated-beadlet formulation having the following composition was prepared as follows.

| Ingredient | | % by Weight of Coated Beadlet |
|---|---|---|
| Core | | |
| Captopril | | 26.2 |
| Citric acid | | 29.1 |
| Microcrystalline cellulose | | 41.8 |
| Film coating | | |
| Hydroxypropylmethyl cellulose phthalate | ca. | 2.6 |
| triethyl citrate | ca. | 0.3 |

The beadlet cores were prepared as described in Example 12.

Hydroxypropylmethyl cellulose phthalate (9 parts) and triethylcitrate (1 part) were dissolved in ethyl alcohol (90 parts) and then sprayed on to the beadlets to form coated product. The so-formed beadlets were then filled into hard shell pharmaceutical capsules which are useful in slowing the progression of atherosclerosis in coronary arteries in hypertensive or normotensive patients and reducing or eliminating coronary atherosclerotic lesions in such patients.

EXAMPLES 15 to 19

Following the procedure of Examples 13 to 15 except substituting the following ACE inhibitor, organic acid and binder-excipients, the following beadlet compositions may be prepared which are useful in slowing the progression of atherosclerosis in coronary arteries in hypertensive or normotensive patients and reducing or eliminating coronary atherosclerotic lesions in such patients.

| Ex. No. | ACE Inhibitor | Organic acid | Binder |
|---|---|---|---|
| 15. | N-(1-ethoxycarbonyl-3-phenyl-propyl)-L-proline | Citric acid | Microcrystalline cellulose |
| 16. | (S)-1-[6-Amino-2-[[hydroxy(4-phenyl-butyl)phosphinyl]-oxy]-1-oxohexyl]-L-proline | Malic acid | Microcrystalline cellulose and hydroxypropyl methyl cellulose |
| 17. | Lisinopril | Tartaric acid | Na carboxymethyl cellulose |
| 18. | Zofenopril | Succinic acid | Gelatin, pectin and Na carboxymethyl cellulose |
| 19. | Fosinopril | Maleic acid | Microcrystalline cellulose |

EXAMPLE 20

By substituting 100 g of pivopril for the zofenopril in Example 11, 1000 tablets each containing 100 mg of the pivopril are produced which is useful in slowing the progression of atherosclerosis in coronary arteries in hypertensive or normotensive patients and reducing or eliminating coronary atherosclerotic lesions in such patients.

EXAMPLE 21

1000 tablets each containing 200 mg of YS890 are produced from the following ingredients:

| YS890 | 200 g |
|---|---|
| Lactose | 100 g |
| Avicel | 150 g |
| Corn starch | 50 g |
| Magnesium stearate | 5 g |

The YS890, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in slowing the progression of atherosclerosis in coronary arteries in hypertensive or normotensive patients and reducing or eliminating coronary atherosclerotic lesions in such patients.

EXAMPLE 22

The following experiment was carried out to study the effect of captopril on the development of atherosclerosis in artherosclerotic cynomolgus monkeys.

SUMMARY

The effect of 6 months treatment with captopril on the development of atherosclerosis in the cholesterol fed cynomolgus monkey was studied. The results obtained show that captopril slowed the development of atherosclerosis. The progression of atherosclerosis in the carotid artery, in the abdominal aorta and in the coronary arteries was dramatically reduced in the captopril-treated animals. The doses of captopril that were used did not change the total serum cholesterol levels significantly and had no effect on the Total Cholesterol/HDL ratio.

METHODS

Animals: A group of 24 feral adult male cynomolgus monkeys, weighing approximately 3.5 kg, were used. All monkeys were given a pretreatment clinical evaluation which included measurement of indirect blood pressure, total serum cholesterol, HDL, and triglycerides.

Treatment: The monkeys were randomly divided into 4 groups of 6 animals per group. A "CONTROL" group of 6 monkeys was given a standard primate diet. The remaining three groups were maintained on a high cholesterol diet, containing a total of 2% cholesterol and 20% fat, for a 6 month period. The "CONTROL" and the "HIGH CHOLESTEROL" groups were given an oral placebo dose twice daily. The "LOW CAPTOPRIL" group was dosed with captopril 25 mg/kg (p.o.) twice daily and the "HIGH CAPTOPRIL" group with 50 mg/kg (p.o.) twice daily. Food and drug consumption was monitored daily.

Blood Pressure Measurement: Indirect blood pressure was measured prior to treatment, and at 3 and 6 months after treatment began. Blood pressure measurements were taken 5 to 10 minutes following an intramuscular injection of ketamine (10 mg/kg), using a Critikon Dinamap Vital Signs Monitor. Measurements were made 1.5-2 hours after captopril administration.

Blood Sampling: Blood samples were taken at 1, 3, and 5 months (1 and 16 hours after dosing) to determine plasma levels of captopril. Additional blood samples were taken at 2, 4, and 6 months for determination of total serum cholesterol, serum HDL, and serum triglycerides.

Necropsy: The monkeys were necropsied after 6 months. A surgical anesthesia was established using sodium pentobarbital (25 mg/kg). The abdominal aorta was clamped and the iliac arteries were removed and placed in physiological solution for in vitro studies of endothelium related relaxation. Following removal of the iliac arteries the animals were flushed with saline using a perfusion pressure of 100 mmHg. The heart was removed and pressure fixed with formalin at 100 mmHg. The thoracic and abdominal aorta, with the internal and external carotid arteries attached, were removed and placed in saline.

Vascular Tissue Preparation: Excess adventitia was removed from the aorta and carotid arteries. A longitudinal cut was made along the dorsal side of the entire vessel and the lumen surface photographed for later surface area measurements. The excised vasculature was then studied as three separate entities:

carotid arteries: Beginning at the origin of the brachiocephalic artery and ending one centimeter distal to the bifurcation of the internal and external carotid arteries.

thoracic aorta: Beginning proximal to the scar of the ligamentum arteriosum an ending at the origin of the celiac artery.

abdominal aorta: Beginning at the origin of the celiac artery and ending at the iliac bifurcation.

One carotid artery, a 5 mm section of the thoracic aorta (immediately proximal to the beginning of the intercostal arteries), and ½ of the abdominal aorta (cut longitudinally) were laid flat and fixed in formalin for later histological processing. The other carotid artery, and the remainder of the thoracic and abdominal aorta were frozen and used for determination of total tissue cholesterol.

The perfused heart was stored in formalin for later histological processing of the following coronary arteries: right coronary, left circumflex, and the left anterior descending.

Gross Pathology: The area of the lumen surface, covered by fatty streaks and plaques, were quantitated from the photographs taken at necropsy. Fatty streaks were defined as "opaque areas of flecks or dots not raised above the plane of the intimal surface." Fatty plaques were defined as "raised atherosclerotic lesions without a fibromuscular cap and with no suggestion of a pearly appearance." Fibrous plaques were defined as "raised atherosclerotic lesions with a grossly evident fibromuscular component and visually appearing pearly."

Histopathology: Cross sections of the formalin fixed tissues were prepared for light microscopy using standard histological techniques. Slides were stained for elastin using aldehyde-fuchsin. Measurements of media area and intima area were made using image analysis. From these measurements the severity of atherosclerosis was determined by calculating the % intimal lesion as follows: % intimal lesion = (intimal area × 100)/internal elastic lamina (IEL) area.

Tissue Cholesterol Determination: Lipids were extracted using standard chloroform/methanol extraction procedures.

Remarks: One monkey (#29) in the Control Group (normal diet) developed respiratory problems midway through the study and was subsequently euthanized. The final diagnosis indicated bronchopneumonia and pulmonary paragonimiasis.

One monkey (#45) in the High Captopril Group was considered a statistical outliar and has been excluded from the statistical evaluation of Gross Pathology (Table 3) and Histopathology (Tables 4 and 5). The actual values for monkey #45 are shown below the tables.

RESULTS

Blood Pressure: The high dose of captopril reduced the blood pressure significantly in these normotensive monkeys at 3 and 6 months; the low dose of captopril reduced blood pressure at 6 months. The high cholesterol diet had no effect on blood pressure (Table 1).

TABLE 1

| | ARTERIAL BLOOD PRESSURE (mmHg) | | | | | |
|---|---|---|---|---|---|---|
| | Pre-Treatment | | 3 Months | | 6 Months | |
| Group | Systolic | Diastolic | Systolic | Diastolic | Systolic | Diastolic |
| Normal Control[a] | 99 ± 3 | 53 ± 3 | 97 ± 3 | 46 ± 1 | 96 ± 5 | 49 ± 5 |
| High Cholesterol | 95 ± 3 | 52 ± 3 | 95 ± 2 | 46 ± 1 | 100 ± 3 | 49 ± 2 |
| Low Captropril | 93 ± 6 | 51 ± 3 | 91 ± 5 | 44 ± 2 | 87 ± 2[c] | 39 ± 1* |
| High Captopril | 95 ± 4 | 54 ± 4 | 75 ± 2* | 33 ± 2* | 74 ± 4* | 33 ± 3* |

Mean ± SEM: N = 6
[a]N = 5 (Monkey #29 died from pulmonary paragonimiasis)
*significantly different from the control group an the high cholesterol group ($p < 0.05$)
[c]significantly different from the high cholesterol group but not from the control group ($p < 0.05$)

Heart Rate: Heart rate varied between approximately 140-160 bpm and was not affected by captopril nor by the high cholesterol diet.

Serum Lipids: The cholesterol diet significantly elevated total serum cholesterol and significantly reduced the serum HDL levels when compared to control levels (Table 2). Although both the total serum cholesterol levels and serum HDL levels were slightly lower in the captopril treated groups as compared to the high cholesterol group these differences were not statistically significant. Serum triglyceride levels did not change during the treatment period.

TABLE 2

| | SERUM LIPID CONCENTRATIONS (mg/dl) | | | |
|---|---|---|---|---|
| Group | Serum Cholesterol (mg/dl) | Serum HDL (mg/dl) | Serum Triglycerides (mg/dl) | Total Chol/ HDL Ratio |
| Norm. Controls[a] | 101 ± 10 | 45 ± 5 | 23 ± 2 | 2 ± 0 |
| High Cholesterol | 706 ± 65 | 24 ± 3 | 17 ± 2 | 33 ± 7 |
| Low Captopril | 566 ± 66 | 22 ± 3 | 15 ± 5 | 27 ± 5 |

TABLE 2-continued

| | SERUM LIPID CONCENTRATIONS (mg/dl) | | | |
|---|---|---|---|---|
| Group | Serum Cholesterol (mg/dl) | Serum HDL (mg/dl) | Serum Triglycerides (mg/dl) | Total Chol/ HDL Ratio |
| High Captopril | 605 ± 55 | 16 ± 2 | 12 ± 2 | 35 ± 5 |

The figures shown are mean (± SEM) from all measurements made during the treatment period (see Blood Sampling in Methods); N = 6
[a]N = 5 (Monkey #29 died from pulmonary paragonimiasis)
No significant differences were found between the high cholesterol group and the two captopril dosed groups ($p < 0.05$).

Plasma captopril concentrations were analysed. Captopril plasma concentrations, 1 hour after dosing, were approximately 3 μg/ml in the low dose group and 6 μg/ml in the high dose group. By 16 hours plasma concentrations were approximately 1 μg/ml and 2 μg/ml for the low and high dose groups respectively.

Gross Pathology (carotid artery): The areas of the lumen surface that were covered with fatty streaks and plaques were calculated and the data expressed as percent of total lumen surface area (Table 3). There were no grossly visible fibrous plaques in the carotid arteries of any animal. The results shown here are from the right carotid artery. Similar data was obtained from the left carotid.

TABLE 3

| | GROSS PATHOLOGY: Right Carotid Artery | | | |
|---|---|---|---|---|
| Group | Vessel Surface (mm$^2$) | % Surface with Lesions | % Surface with Fatty Streaks | % Surface with Fatty Plaques |
| Norm. Controls[a] | 112.0 ± 8.4 | 0.0 ± 0.0 | 0.0 ± 0.0 | 0.0 ± 0.0 |
| High Cholestrol | 125.3 ± 10.1 | 46.4 ± 6.2 | 14.5 ± 4.5 | 31.9 ± 7.0 |
| Low Captopril | 114.1 ± 8.4 | 22.3 ± 6.1* | 14.2 ± 4.8 | 8.1 ± 5.7* |
| High Captopril[b] | 120.5 ± 10.1 | 13.7 ± 6.2* | 10.8 ± 6.6 | 2.9 ± 2.2* |

Mean ± SEM; N = 6
[a]N = 5 (Monkey #29 died from pulmonary paragonimiasis)
[b]N = 5 (Monkey #45 was excluded as a statistical outliar. The "% Surface with lesions" was 100%.)
*significantly different from the high cholesterol group ($p < 0.05$)

Histopathology (carotid arteries and aortic segments): The following arteries, from the high cholesterol-placebo group all showed significant increases in % intimal lesion when compared to the normal diet (control) group: carotid bifurcation (CB), common carotids (CC), and the abdominal aorta (AA), and thoracic aorta (TA) (Table 4). Lesions in the carotid bifurcation were more severe than in the other three arterial segments measured. However, the high dose of Captopril (50 mg/kg, BID) reduced lesions by over 50%; the lower dose of captopril (25 mg/kg, BID) reduced the % intimal lesion by 36%. A significant reduction in lesion area was also seen in the common carotid artery and the abdominal aorta. The thoracic aorta (TA) had less severe lesions than the other arterial segments studied; the effect of captopril was not significant.

Histopatholoqy (coronary arteries): % intimal lesion was measured in the Right Coronary artery (RCA), the left Circumflex artery (LCX), and the Left Anterior Descending artery (LAD). In the control animals (normal diet) the intimal area was so thin it could not be measured accurately using a 10× objective. The high cholesterol diet resulted in significant lesion development in all three coronary arteries studies (Table 5). The high dose of captopril totally prevented lesions from developing in the RCA and caused a significant reduction in lesion development in both the LCX and the LAD. The low dose of captopril also reduced lesion formation in all three coronary arteries but the reduction was only significant in the LAD.

TABLE 5

| | PERCENT INTIMAL LESION: Coronary Arteries | | |
|---|---|---|---|
| Group | Right Coronary | Left Circumflex | Left Anterior Descending |
| Norm. Controls[a] | 0.0 ± 0.0 | 0.0 ± 0.0 | 0.0 ± 0.0 |
| High Cholesterol | 5.9 ± 2.3[c] | 13.4 ± 4.6[c] | 6.2 ± 1.0[c] |
| Low Captopril | 4.1 ± 2.6 | 5.5 ± 3.7 | 1.6 ± 1.3* |
| High Captopril[b] | 0.0 ± 0.0* | 0.9 ± 0.6* | 0.1 ± 0.1* |

Mean ± SEM: N = 6
[a]N = 5 (Monkey #29 died from pulmonary paragonimiasis)
[b]N = 5 (Monkey #45 was excluded as a statistical outliar. The intimal lesions for this animal were 0.0% and 43.2% for the RCA and LCX respectively; lesions in the LAD were not determined in this animal.
*significantly different from the high cholesterol group ($p < 0.05$)
[c]significantly different from the control group ($p < 0.05$)

TABLE 4

| | PERCENT INTIMAL LESION: Carotid Arteries and Aortic Segments | | | |
|---|---|---|---|---|
| Group | Carotid Bifurcation | Common Carotid | Thoracic Aorta | Abdominal Aorta |
| Norm. Controls[a] | 2.6 ± 1.7 | 0.2 ± 0.1 | 0.0 ± 0.0 | 0.1 ± 0.1 |
| High Cholesterol | 55.7 ± 10.8[c] | 13.6 ± 3.6[c] | 5.9 ± 2.5 | 9.0 ± 2.3[c] |
| Low Captopril | 32.7 ± 9.4[c] | 2.7 ± 1.1* | 5.2 ± 2.0 | 4.7 ± 1.9 |
| High Captopril[b] | 18.8 ± 7.7* | 0.6 ± 0.4* | 3.7 ± 2.0 | 2.9 ± 1.1* |

Mean ± SEM; N = 6
[a]N = 5 (Monkey #29 died from pulmonary paragonimiasis)
[b]N = 5 (Monkey #45 was excluded as a statistical outliar. The intimal lesions for this animal were 53.8%, 37.5%, 8.0%, 31.0% for the CB, CC, TA and AA respectively.)
*significantly different from the high cholesterol group ($p < 0.05$)
[c]significantly different from the control group ($p < 0.05$)

CONCLUSIONS

The primary purpose of this study was to determine if oral administration of captopril inhibited the development of atheroslerosis in the cholesterol fed cynomolgus monkey. Results obtained indicate that captopril slowed the progression of atherosclerosis. Thus, in the study, it was found that the intimal lesions in the carotid arteries and in the abdominal and thoracic aorta were reduced in the captopril-treated animals. However, intimal lesions in the coronary arteries were dramatically eliminated in the captopril-treated animals.

What is claimed is:

1. A method for stabilizing or causing regression of othersclerosis in the coronary arteries in a normotensive patient, which comprises administering to a normotensive patient in need of such treatment on effective amount of an angiotensin converting enzyme inhibitor wherein said inhibitor is administered is single or divided doses of from about 0.1 to about 500 mg/one to four times daily over a prolonged period of treatment.

2. The method as defined in claim 1 wherein atherosclerotic lesions in the coronary arteries are stabilized or made to regress.

3. The method as defined in claim 1 wherein the angiotensin converting enzyme inhibitor is a mercapto containing ACE inhibitor.

4. The method as defined in claim 1 wherein the angiotensin converting enzyme inhibitor is a substituted proline derivative.

5. The method as defined in claim 1 said angiotensin converting enzyme inhibitor is administered orally or parenterally.

6. The method as defined in claim 1 wherein said angiotensin converting enzyme inhibitor includes a mercapto moiety and is a substituted proline derivative.

7. The method as defined in claim 1 wherein said angiotensin converting enzyme inhibitor is a substituted proline derivative.

8. The method as defined in claim 1 wherein said angiotensin converting enzyme inhibitor is captopril.

9. The method as defined in claim 1 wherein said angiotensin converting enzyme inhibitor is zofenopril.

10. The method as defined in claim 1 wherein said angiotensin converting enzyme inhibitor is fentiapril.

11. The method as defined in claim 1 wherein the angiotensin converting enzyme inhibitor is a phosphonate substituted amino or imino acid or salt thereof, a proline derivative, a substituted proline derivative, a mercaptoacyl derivative of a substituted proline, a carboxyalkyl dipeptide derivative, a phosphinylalkanoyl proline derivative or a phosphonamidate derivative.

12. The method as defined in claim 11 wherein said angiotensin converting enzyme inhibitor is a carboxyalkyl dipeptide derivative.

13. The method as defined in claim 1 wherein said angiotensin converting enzyme inhibitor is a phosphinylalkanoyl proline derivative, a phosphoramidate derivative, or a phosphonate substituted amino or imino acid or salt thereof.

14. The method as defined in claim 13 wherein said angiotensin converting enzyme inhibitor is captopril or zofenopril.

15. The method as defined in claim 1 wherein said angiotensin converting enzyme inhibitor is enalapril or lisinopril.

16. The method as defined in claim 1 wherein said angiotensin converting enzyme inhibitor is fosinopril or (S)-1-[6-amino-2-[[hydroxy(4-phenylbutyl)phosphinyl]oxy]-1-oxohexyl]-L-proline (ceranapril).

17. The method as defined in claim 1 wherein said angiotensin converting enzyme inhibitor is administered in the form of tablets, capsules or by injection.

18. The method as defined in claim 1 wherein said angiotensin converting enzyme inhibitor is captopril or zofenopril and is administered systemically in an amount of from about 0.1 to about 500 mg/one to four times a day.

* * * * *